United States Patent [19]

Prough et al.

[11] Patent Number: 4,626,318

[45] Date of Patent: * Dec. 2, 1986

[54] METHOD OF CONTROLLING A PULP REFINER BY MEASURING FREENESS AND REMOVING THE LATENCY FROM THE PULP

[75] Inventors: James R. Prough; James E. Morin, both of Glens Falls, N.Y.

[73] Assignee: Kamyr, Inc., Glens Falls, N.Y.

[*] Notice: The portion of the term of this patent subsequent to Jun. 24, 2003 has been disclaimed.

[21] Appl. No.: 754,739

[22] Filed: Jul. 15, 1985

[51] Int. Cl.$^4$ ............... D21D 1/20; D21D 5/20
[52] U.S. Cl. ............... 162/49; 162/52; 162/61; 162/254
[58] Field of Search ............... 162/49, 59, 1, 100, 162/261, 263, 198, 259, DIG. 10, 57, 61, 254, 253, 52; 55/21

[56] References Cited

U.S. PATENT DOCUMENTS 4,361,464 11/1982 Karnis ............... 162/49
4,435,193 3/1984 Gulichsen et al. ............... 55/21

FOREIGN PATENT DOCUMENTS 1054416 5/1979 Canada ............... 162/49

OTHER PUBLICATIONS

Dawson et al, "A Method for Developing Latent Properties of Mechanical Pulps," vol. 79, No. c, p. 81, *Pulp & Paper Canada*.

TMPCON: Thermo-Mechanical Pulping Control—A Modern Means of Controlling Pulp Quality, pp. 2, 3, 4.

DRT—EUR-Control In-Line Refining Analyzer for Analysis of the Refining Result (EUR-Control D 218.35/1-e·a).

*Primary Examiner*—Steve Alvo
*Attorney, Agent, or Firm*—Nixon & Vanderhye

[57] ABSTRACT

Immediate and accurate control of a pulp refiner is provided so as to control the degree of refining in the production of mechanical pulp, such as RMP, TMP, and CTMP. The mechanical pulp discharged from a refiner is fluidized by a fluidizing centrifugal pump, the fluidizing action instantaneously removing the pulp latent properties. A sample of the latency-removed pulp is then subjected to a pulp freeness measurement, and that freeness measurement is supplied to a computer. The computer utilizes the freeness measurement, as well as other measurements such as pulp consistency and flow rate measurements, and dilution flow measurements, and in response to the inputs control refiner parameters to ensure that the freeness of the mechanical pulp being produced is within the desired range. The refiner parameters controlled can be the hydraulic plate loading (refining pressure), and/or the tonnage of fiber supplied to the refiner.

9 Claims, 1 Drawing Figure

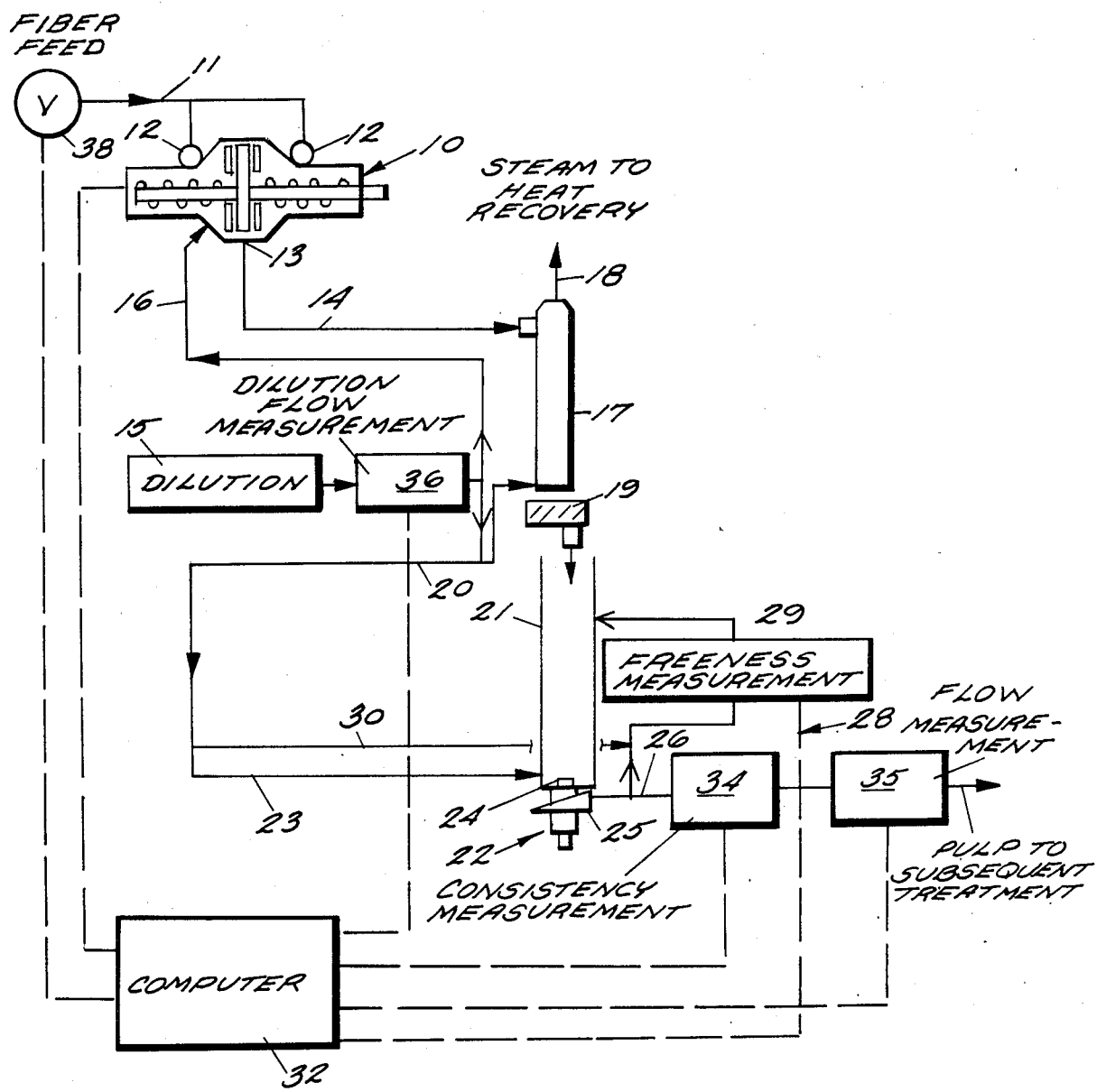

METHOD OF CONTROLLING A PULP REFINER BY MEASURING FREENESS AND REMOVING THE LATENCY FROM THE PULP

BACKGROUND AND SUMMARY OF THE INVENTION

In the production of mechanical pulps, such as TMP, CTMP, and RMP, it is necessary to refine the pulp sufficiently so that it can be used for its intended purposes. The degree of refining is commonly measured by measuring the "freeness" of the mechanical pulp. The freeness is a measure of how water drains from a pulp water mixture.

In conventional mechanical pulp producing systems, freeness is sometimes determined immediately after refining, and based upon the freeness measurements various refiner parameters are controlled to adjust the degree of refining provided by the refiner. For instance in some installations a conventional freeness measurement instrument, such as a DRT Freeness Measuring Instrument, available from Eur Control USA, Inc. of Decatur, Ga., is operatively disposed directly in the discharge line from the refiner (or the last refiner in the sequence of refiners). However accurate control of freeness does not ensue when utilizing such systems since the latent properties of the pulp interfere with the accurate measurement of freeness. In order to overcome this problem, a number of installations use conventional mixing and soaking chests, commonly referred to as "latency chests", to effect latency removal. Freeness is then measured after the latency removal. However since latency removal utilizing such procedures typically takes about 45 minutes to an hour, and because of this resulting delay, immediate control of the refiner is not possible. Therefore there can be substantial production of mechanical pulp that does not have the desired degree of refining.

According to the present invention, immediate and accurate feedback is provided so that the refiner can be controlled precisely to produce mechanical pulp having the desired degree of refining. This allows the production of a maximum amount of pulp having desired properties, and a minimum amount of pulp having undesired properties.

Immediate and accurate feedback control according to the invention is obtained by taking advantage of the virtually instantaneous removal of the latency of mechanical pulp that can be provided utilizing a fluidizing centrifugal pump, as disclosed in copending application Ser. No. 608,191 filed May 8, 1984, now U.S. Pat. No. 4,596,631, and the disclosure of which is hereby incorporated by reference herein. According to the present invention, shortly after refining (e.g. the last refining stage), the mechanical pulp is fluidized by a fluidizing centrifugal pump to effect removal of the mechanical pulp latent properties, and then a sample of the latency-removed pulp is selected and subjected to freeness measurement. The values of the freeness measurements, as well as other measured parameters such as consistency and flow measurements, are fed to a computer. The computer controls various refiner parameters in response to these measurements. For instance the computer controls the feed of comminuted cellulosic fibrous material to the refiner, and/or the hydraulic plate loading of the refiner (refining pressure) so as to adjust the degree of refining of the mechanical pulp produced. In this way mechanical pulp is produced having the desired degree of refining, as determined by the freeness of the pulp, in a quick and accurate manner. This maximizes the production of pulp having desired properties and minimizes the production of pulp with undesired properties.

It is the primary object of the present invention to provide a method and apparatus for the immediate accurate feedback control of a pulp refiner in the production of mechanical pulp. This and other objects of the invention will become clear from an inspection of the detailed description of the invention, and from the appended claims.

BRIEF DESCRIPTION OF THE DRAWING

The drawing FIGURE schematically illustrates exemplary apparatus according to the present invention for immediately and accurately controlling the degree of refining of mechanical pulp.

DETAILED DESCRIPTION

The invention is applicable to the production of all types of mechanical pulp, including RMP, TMP, and CTMP. For simplicity, however, FIG. 1 merely illustrates exemplary apparatus utilized in the production of RMP. In the production of TMP, CTMP, and other types of mechanical pulps, various other apparatus would be provided either prior or subsequent to the refiner.

In the drawing, a conventional pulp refiner is illustrated generally by reference numeral 10. While in the drawing only one refiner stage is shown, two or more refiner stages may be provided, as is conventional. Comminuted cellulosic material is fed in line 11 to inlets 12 to the refiner 10, and the mechanical pulp produced is discharged from discharge 13 of the refiner 10 into discharge line 14. As is conventional dilution liquid is added to the refiner 10 as required from dilution source 15 through line 16. The mechanical pulp in line 14 is typically led to a cyclone separator 17, or the like, and the steam produced during the refining action is recovered through line 18 while the pulp itself passes to mixer 19. Dilution liquid from source 15 also can be added to the pulp at the mixer 19 through line 20.

Soon after refining, according to the invention the pulp is subjected to fluidizing action to remove the latent properties from the pulp. This is preferably accomplished by feeding the pulp from mixer 19 to a pump surge tube 21 which has a fluidizing centrifugal pump 22 at the bottom thereof. A typical such pump is described in said U.S. Pat. No. 4,596,631, and is also shown in U.S. Pat. No. 4,435,193. Preferably dilution liquid from source 15 is added via line 23 to the tube 21 just prior to the pump 22 so that the consistency of the pulp while being pumped by the pump 22 is in the range of about 8–25%, preferably about 10–15%. As the pulp passes from the inlet 24 to pump 22 to the outlet 25 of the pump 22, the fluidizing action that it is subjected to essentially instantaneously (usually in about 0.4–0.8 seconds) removes the latency of the pulp. The essentially latency free mechanical pulp is then discharged into line 26.

According to the present invention, a portion (a sample) of the pulp in line 26 is continuously removed into a recycle loop, shown generally by reference numeral 28. As seen in the drawing, the recycle loop 28 is operatively connected between the outlet 25 of the pump 22 and the inlet 24 thereof, typically having one end connected downstream of the outlet 25 in line 26, and having the other end connected to the tube 21. Disposed within the recycle loop 28 is a conventional freeness measurement apparatus 29, such as a Model DRT Refining Analyzer sold by Eur-Control USA, Inc. of Decatur, Ga. Depending upon the particular instrument 29 utilized, it may be necessary to further dilute the pulp sample (e.g. to 6% consistency) in order to get an effective measurement, and this is accomplished by adding dilution liquid from source 15 through line 30 directly into the recycle loop 28 prior to the instrument 29.

Refiner control means are operatively connected to the freeness measurement means 29 and the refiner 10 for operatively controlling the refiner 10 in response to the freeness measurements from the device 29. Preferably such refiner control means includes a computer 32. In order for the computer 32 to accurately control the refiner 10 in order to achieve the desired degree of refining, in addition to the freeness measurement from the device 29, the computer also needs production, dilution flow, and wood moisture inputs, or the like. Production can be calculated from pulp flow and consistency measurements, while the dilution flow and the freeness can be measured directly. All these inputs are shown operatively connected to the right-hand side of the diagrammatic representation of the computer 32 in the drawing.

Pulp consistency and flow measurements, used by the computer 32 to calculate production, are preferably taken in the discharge line 26 from the pump 22. A conventional consistency measurement device 32, and a conventional flow measurement device 35 are disposed directly in the line 26 downstream from the recycle loop 28. Dilution flow measurement can be determined utilizing a conventional dilution flow measuring device 36 operatively connected to the dilution source 15.

A computer 32 typically will control one, or both, of two refiner parameters. As illustrated schematically in the drawing, the computer is operatively connected to controls for the refiner 10 to control the hydraulic plate loading (refining pressure) for the refiner 10. The computer also can control the specific loading by controlling the tonnage, that is by controlling valve 38 which controls the feed of the fiber to the refiner 10. Where multistage refining is practiced, the computer 32 can control the tonnage and/or hydraulic plate loading for one or all refiners.

It will thus be seen that according to the present invention immediate feedback control of the refiner 10 is practiced so as to control the degree of refining. Though the feedback control is immediate it is still accurate since the latent properties of the mechanical pulp have been removed prior to the freeness measurement which is fed to the controlling computer. Thus according to the invention it is possible to minimize the amount of mechanical pulp having undesired properties that is produced, while maximizing the amount of pulp having the desired degree of refining.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent methods and apparatus.

What is claimed is:

1. A method of controlling a refiner which refines comminuted cellulosic fibrous material to produce mechanical pulp having latent properties, comprising the steps of:
    (a) fluidizing mechanical pulp having a consistency of about 8-25 percent shortly after discharge from the refiner so as to effect substantially complete removal of the latency thereof, by, and during, centrifugal pumping of the pulp while it has a consistency of about 8-25 percent in a generally non-return path;
    (b) continuously measuring freeness of a sample of the latency-removed pulp, and wherein the only portion of the pulp not passing in the non-return path is the sample, the sample being recirculated after freeness measurement; and
    (c) in response to the measurement obtained in step (b), automatically controlling refiner parameters to ensure the mechanical pulp produced has desired freeness properties.

2. A method as recited in claim 1 wherein step (c) is practiced by controlling the specific loading of the refiner.

3. A method as recited in claim 2 wherein the specific loading controlling is provided by controlling the tonnage of cellulosic material supplied to the refiner, and/or by controlling the refining pressure.

4. A method as recited in claim 3 wherein step (c) is further practiced by measuring the consistency and the flow of the latency-removed mechanical pulp, and feeding the consistency and flow measurements, as well as the freeness measurement from step (b), to a computer which operatively controls the refiner parameters.

5. A method as recited in claim 4 comprising the further step of diluting the mechanical pulp prior to practice of step (a) so that it has a consistency of between about 8-25% when it is fluidized.

6. A method as recited in claim 5 comprising the further step of diluting the mechanical pulp sample utilized in the practice of step (b) so that it has a lower consistency than the pulp during fluidization thereof.

7. A method as recited in claim 1 wherein step (c) is further practiced by measuring the consistency and the flow of the latency-removed mechanical pulp, and feeding the consistency and flow measurements, as well as the freeness measurement from step (b), to a computer which operatively controls the refiner parameters.

8. A method as recited in claim 1 comprising the further step of diluting the mechanical pulp prior to practice of step (a) so that it has a consistency of between about 8-25% when it is fluidized.

9. A method as recited in claim 8 comprising the further step of diluting the mechanical pulp sample utilized in the practice of step (b) so that it has a lower consistency than the pulp during fluidization thereof.

* * * * *